United States Patent [19]

Krupa et al.

[11] 4,140,011

[45] Feb. 20, 1979

[54] AUTOMATIC PRECIPITATION SAMPLER

[75] Inventors: Sagar V. Krupa, Arden Hills; Michael R. Coscio, Minneapolis; Donald B. McIntyre, St. Paul; Donald I. Frisbie, Minneapolis; Robert L. Howard, St. Paul, all of Minn.

[73] Assignee: The Regents of the University of Minnesota, Minneapolis, Minn.

[21] Appl. No.: 801,966

[22] Filed: May 31, 1977

[51] Int. Cl.² ............................................. G01W 1/14
[52] U.S. Cl. ................................... 73/171; 73/421 R; 141/130
[58] Field of Search .............. 73/171, 421 R; 141/130

[56] References Cited

U.S. PATENT DOCUMENTS 3,296,858  1/1967  Doury et al. ........................ 73/171

FOREIGN PATENT DOCUMENTS

1211627  3/1960  France ........................ 73/171

*Primary Examiner*—Donald O. Woodiel
*Attorney, Agent, or Firm*—Jones, Tullar & Cooper

[57] ABSTRACT

An automatic precipitation sampler contains a precipitation detector which signals a control system to remove a cover above the collector surface at initiation of precipitation. Water flows from the inert collector surface, through a sample distributor having an inert surface, to a storage means. The cover is replaced over the collector at the termination of the precipitation event and the storage means is automatically sealed to prevent contamination and evaporation. The time of initiation of sampling and duration of sample collection are measured with a digital clock and stored in memory for later retrieval. Multiple storage means attached to a sequencing sample distributor permit collection of samples from a number of separate events or multiple samples from the same event. Power to operate the system is obtained from a battery and compressed gas making possible operation in remote locations for long intervals.

7 Claims, 12 Drawing Figures

AUTOMATIC PRECIPITATION SAMPLER

BACKGROUND OF THE INVENTION

1. Field of the Invention

The invention provides a means for automatically obtaining water samples from precipitation events which are to undergo analysis for trace chemical constituents. The sampler can operate unattended for long periods and collect multiple samples in sealed bottles of inert plastic. The time of sampling and duration of sampling are both recorded.

The importance of the physio-chemical analysis of rain and other forms of precipitation has become increasingly important as concern over atmospheric pollution mounts and techniques for measuring an ever increasing number of contaminants in smaller concentrations continue to be developed. As in all material analysis, the information is only as good as the quality of the collected sample and the information available from it. Consequently, as the information desired becomes more extensive and more affected by a greater number of variables, the sample collection procedure employed must of necessity become more sophisticated.

Collection of rain samples would appear to be a simple matter. However, the analyst is typically looking for constituents present in concentrations of parts per million or even less; hence, the collection equipment must be very clean and all surfaces which come in contact with the sample should be of relatively inert material which will not in itself be of a source of contamination.

The exact time of collection of the sample can be of importance in many studies since results can be related to meteoroligical data. The collection site may frequently be relatively inaccessible and it is often desirable to collect only the early part of an extended precipitation event since most of the contaminants which are scrubbed out of the atmosphere will be present in samples collected during the initial period. Consequently, a sampling device which operates automatically and which is capable of recording the time at which the sample was collected is very nearly essential. Concern over the harmful effects of pollution are resulting in an ever increasing number of legal actions; thus, the importance of a sound sampling system cannot be overstated when results of pollution studies are introduced as evidence in the courts.

Prior Art

Papers reporting on results obtained from physio-chemical analysis of rain samples have appeared at least as early as 1926. Thus, some means for collecting rain samples for analysis have been in use for at least 50 years. An evaluation of a number of precipitation samplers is contained in a paper by Galloway and Likens, 1975 Proc. 1st Internat. Symp. on Acid Precipitation and the Forest Ecosystem (1976).

A sampler developed by the Health and Safety Laboratory of the Atomic Energy Commission has provision for automatically uncovering a sample collection funnel at the onset of precipitation and closing it again when precipitation ceases. Thus, this sampler has some of the features cited as important in the context of todays sampling problem. It is, however, deficient on a number of points. Collection surfaces are of metal instead of inert material such as Teflon. There is no provision for collecting individual samples from separate precipitation events; for example, if the sample is not collected after each precipitation, the next event simply adds to water already present in the sample container. There is also no means for collecting a number of separate samples throughout an extended period of continued precipitation. The time of sample collection is not recorded making correlation with available meteorological data very tenuous. Finally, power requirements are relatively high thus requiring a sizeable power pack for unattended operation for long periods.

SUMMARY OF THE INVENTION

It is therefore a principal object of this invention to provide a sampler which is capable of collecting samples of precipitation in the "as fallen" condition for analysis of trace constituents.

It is a related object of the invention to provide a precipitation sampler which is fully automatic and capable of obtaining samples from a number of separate and distinct precipitation events or multiple samples from the same precipitation event completely unattended.

It is another object of the invention to incorporate an adjustable precipitation detector responsive to a predetermined rate of precipitation, i.e. which can discriminate between very light precipitation and more heavy precipitation and thereby to prevent sampling of the former, while permitting a sample of the latter to be collected.

It is still another object of the invention to include means for measuring and recording the chronological and/or lapsed time of one or more of the operations conducted by the apparatus; for example, time measuring means in the sample system which will measure the interval of time from loading empty storage means to initiation of collection of sample and the duration of sample collection; and to include with the time measuring means a recording means which permits retrieval of all time intervals and permits correlation with meteorological data.

Another object of the invention is to provide a precipitation sampler with a collector cover (to seal against dust, insects, pollen, molds, and other sources of contamination) which can be automatically removed when precipitation has commenced, i.e. when a predetermined amount of precipitation has been sensed, and automatically returned when it stops.

Still another object of the invention is to provide an automatic precipitation sampler which can operate unattended for long intervals using a self-contained power source such as a battery and/or compressed gas.

It is yet another object of the present invention to position the collector surface far enough above adjacent surfaces and away from the collector cover to preclude possibility of contamination from splash.

A further object of the invention is the incorporation of a detector funnel and collector surface which contain heating elements affixed to the under surface and which can be automatically energized, i.e., through a pre-set thermal switch, when temperatures dip low enough to cause precipitation to fall as snow.

Still another object of the invention is to provide a collection system in which all wetted surfaces, including sample storage means, are relatively inert to prevent contamination of collected samples.

In accordance with the objects cited above, a novel precipitation sampler is provided which contains an adjustable precipitation detector so designed that the sampler will function only in precipitation above a certain predetermined level of intensity, e.g., to collect or reject drizzle or a light rain, as desired. Water collected in the detector funnel flows into a flow rate detector element, e.g., a tee connection below which is a flow resistive element. An adjustable water level detector is located above the tee connector. The flow resistive element causes water to rise in the leg containing the level sensor. If flow is very low, the level may never actuate the flow rate detector element and there will be no collection of sample. A flow above a predetermined rate will cause the detector to signal a control circuit. The control circuit causes mechanical actuators to function which remove the cover above the collector surface and rotate the sample distributor thus placing a storage means, e.g., a sample bottle in line with flow from the collector. The time interval between the previous movement of the sample distributor and the just completed movement is measured and recorded by the time measuring and recording means and a new measure of time interval is initiated.

On cessation of precipitation, the water level in the detector recedes until the level sensor is uncovered. This signals the control to proceed with return of the collector cover and movement of the sample distributor to the next position which contains a by-pass line. The sample is sealed as a result of movement to a position which has no connection to the atmosphere. The interval of time between movements is again recorded in the recording means and a new time interval is initiated. Each position on the sample distributor is consecutively numbered and the recording means is incremented with each movement of the sample distributor such that later recall of time intervals can be related to distributor position.

DESCRIPTION OF THE PREFERRED EMBODIMENT

Figure 1A:
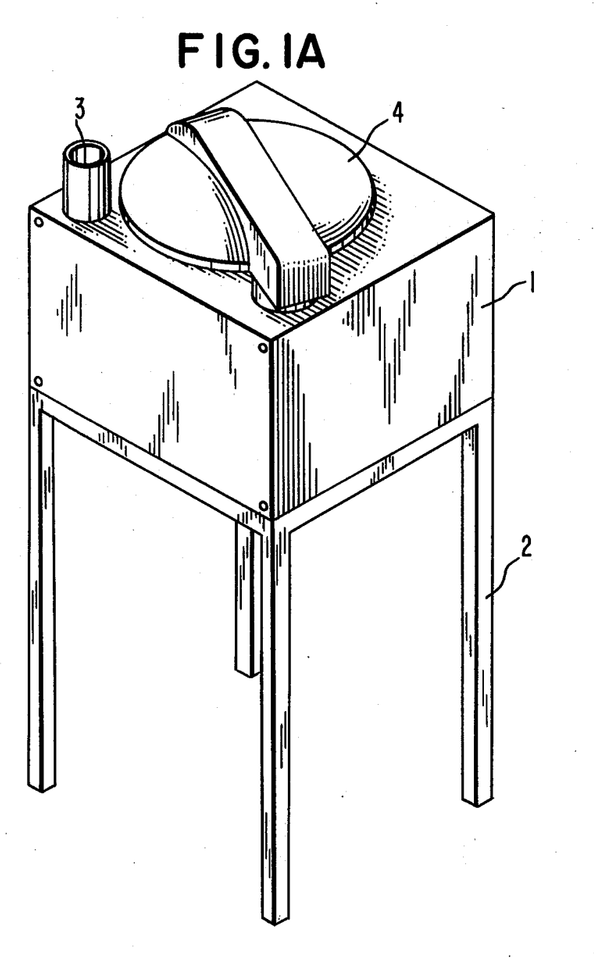
FIGS. 1A and 1B are exterior views of the precipitation sampler showing the detector collection cylinder, collection funnel, and collector cover movement.
Figure 1B:
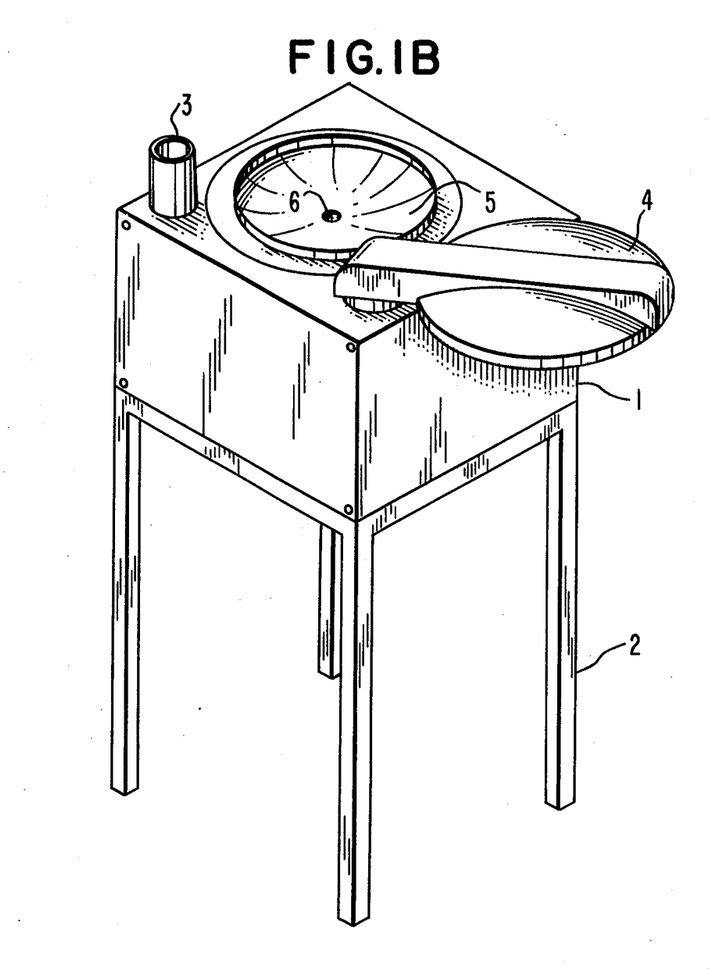

With reference to FIGS. 1A and 1B the automatic precipitation sampler comprises generally an enclosure 1, preferably from a heat reflecting metal, a support structure 2, a precipitation detector 3, a sample collector cover 4 which is automatically rotated at the initiation of precipitation, upon a signal from the detector 3, to expose a sample collection funnel 5, a sample distribution means immediately below the funnel outlet 6, and all necessary controls, actuating mechanism and power sources in the enclosure as required to collect samples of each precipitation event, record the time of sampling, and to seal the collector funnel and sample storage means between precipitation events.

Figures 2, 5:
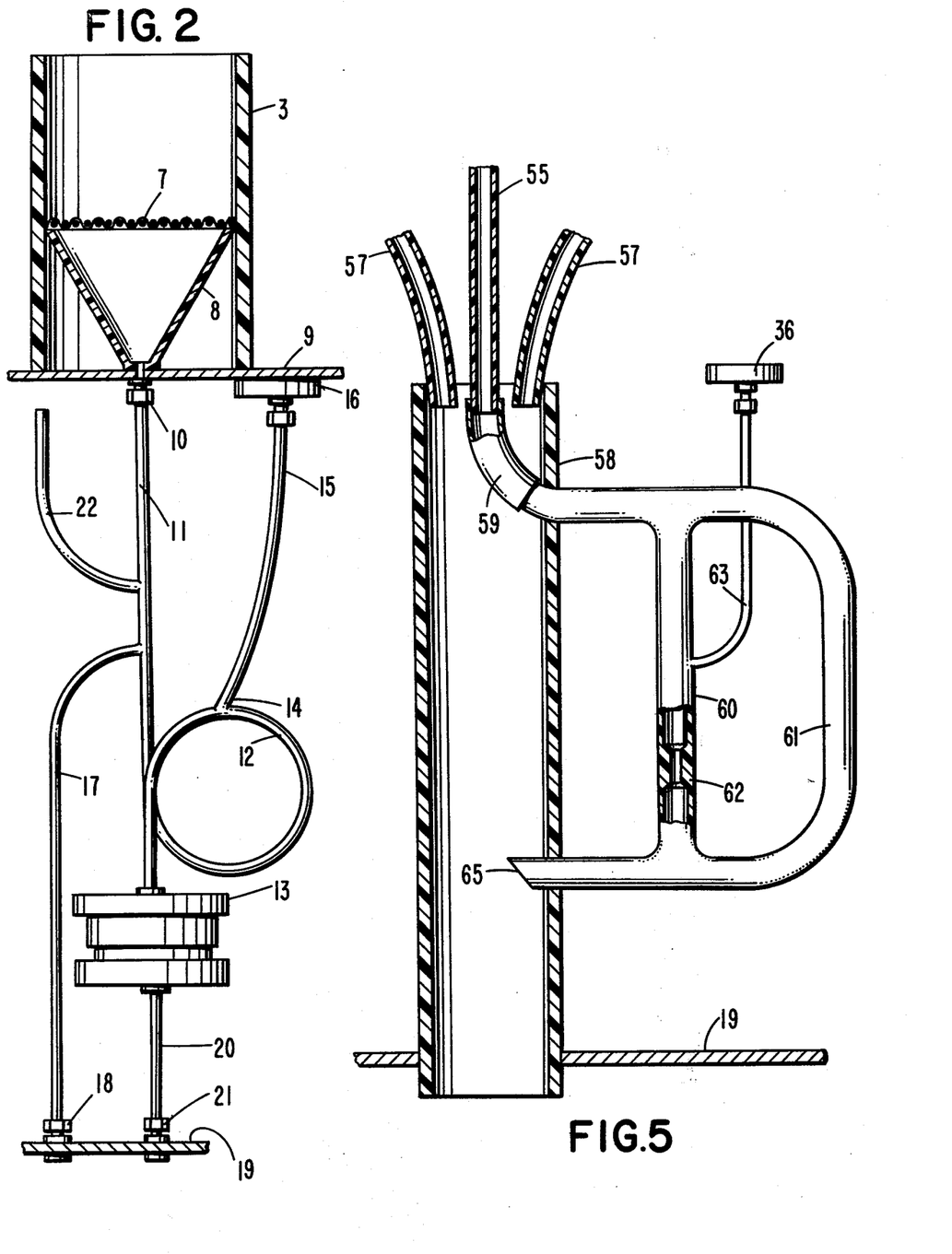
FIG. 2 is a schematic of the precipitation detection system showning the collection funnel, tubing arrangement, pressure switch, and flow restrictive element.
FIG. 5 is a cross-sectional schematic sample turret sump.

Specifically, with reference to FIGS. 1 and 2, the automatic precipitation sampler is as pictured in FIG. 1A when there is no precipitation. When precipitation begins, water is collected in open cylinder precipitation detector 3 and flows through an extraneous solids removal means, e.g., a fine screen 7, into funnel 8 which passes through the top surface plate 9 of the metal enclosure 1 through fitting 10 into tube 11. Tube 11 drops through loop 12, which traps suspended matter not retained by screen 7, to flow-restrictive element 13. As water continues to flow into loop 12, the level rises to tee connection 14 and spills over to flow-restrictive element 13. The flow restrictive device may be a valve, capillary tube, or other similar device; however, in the preferred embodiment of this invention, a fine filter of relatively large area is used to prevent a few small particles from altering the flow resistance significantly. When water passes tee connection 14, air is trapped in tube 15 leading to pressure switch 16. As the level of water rises in tube 11 as a result of the flow restriction in element 13, water also rises in tube 15 causing the pressure in this tube to increase to a level which causes pressure switch 16 to close sending a signal to the control circuit that a significant amount of precipitation has been detected to initiate action which will uncover sample collection funnel 5 as demonstrated in FIG. 1B. When the level of water rises in tube 11 to the point of connection of overflow tube 17, the excess runs through tube 17 and connection 18 through the bottom plate 19 of the metal enclosure 1 to the ground. Water passing through the flow restrictive element 13 is then discharged to the ground through tube 20 and tubing connector 21. Vent tube 22 is attached to tube 11 a short distance above the overflow connection to ensure that atmospheric pressure exists at all times at the surface of the water in tube 11.

Figure 3:
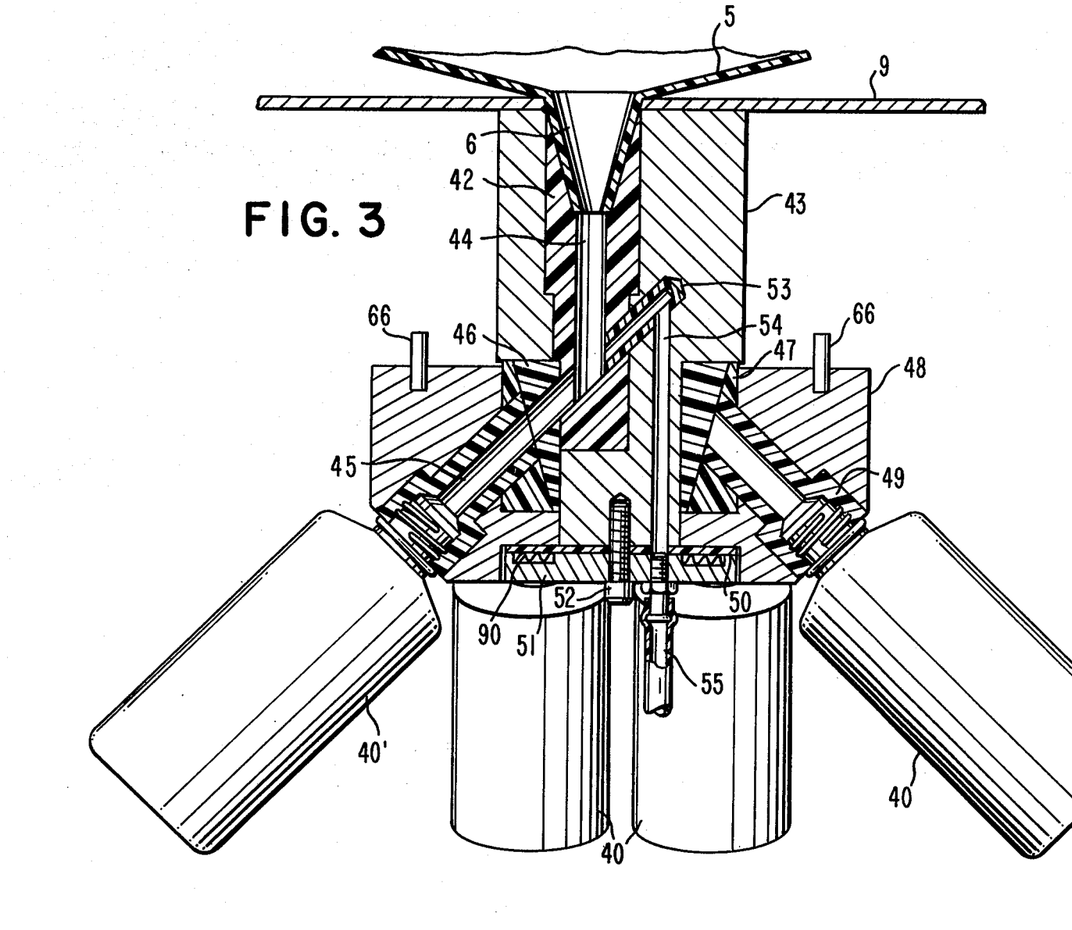
FIG. 3 is a cross-sectional view of the sample-distribution turret.

FIG. 3 shows a cross-sectional view of the sample distribution means, e.g., a sample distribution turret. A sample bottle 40' is shown in the collection position; sample bottle 40 is shown in a sealed position. Starting at the top of the drawing, the outlet 6 of sample collection funnel 5 is attached to a Teflon sleeve 42 which is held by a aluminum block 43 attached to the under side of the top surface plate 9. The cylindrical flow passage 44 in the Teflon sleeve 42 intersects a cylindrical flow passage 45. Teflon insert 47 fits tightly in a movable aluminum cylinder 48, as do eight Teflon cylinders 49 having female threaded ends to accept sample bottles 40. Aluminum disc 51 contains means such as coil springs 90 which compress against the Teflon annular ring 50 to force the movable aluminum cylinder 48 against the conical Teflon insert 46. Disk 51 is attached to the bottom of the cylindrical extension of block 43 by machine screw 52. Cylindrical flow passage 45 is extended upward past the intersection of passage 44 to provide for overflow when a bottle is filled. Teflon insert 53 is inserted in the overflow extension to ensure that all water which could possibly find its way into a sample bottle is in contact with an inert surface. Flow passage 54 is drilled into block 43 and intersects flow passage 45 through Teflon insert 53 and connects to an overflow tube 55 at the bottom to complete the overflow section of the turret.

Figure 4:
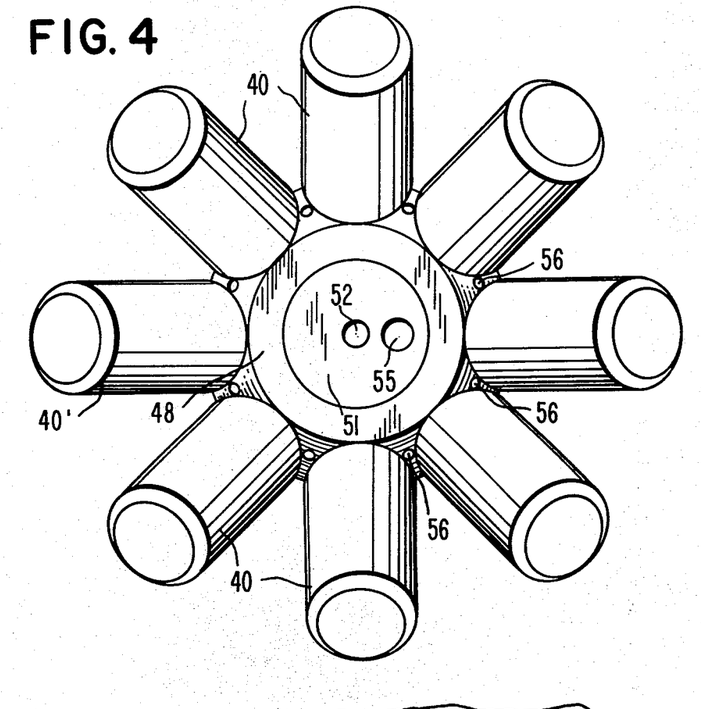
FIG. 4 is a view of the sample-distribution turret from below which shows the arrangement of eight sample bottles.

FIG. 4 is a view of the sample-distribution turret from below which shows the arrangement of eight sample bottles 40. Eight holes 56, spaced between the sample bottles, connect to drain tubes. If a sample bottle is not in a collection position, one of these drain tubes is, so that any residual water in the collection system is drained before the next bottle is moved into position.

FIG. 5 is a cross-sectional view of sample turret sump. The overflow tube 55 and eight drain tubes 57 enter the top section of tube 58 which passes through the bottom plate 19 of the sampler enclosure. Water from drain tubes 57 drops straight through tube 58 to ground; however, overflow tube 55 enters elbow 59 which is connected to parallel tubes 60 and 61. The water from the overflow tube 55 enters tube 60 which contains a short capillary restriction 62 which causes the water to back up trapping air in tube 63. As water rises farther in tube 60, the pressure in tube 63 increases causing the overflow pressure switch 36 to close. Closing of the overflow pressure switch 36 informs the electronic controller 23 that a sample bottle is full. The controller then initiates action to move the turret another step which seals the filled bottle and moves a drain tube 57 into the collecting position. If water flows at a rate sufficient to completely fill tube 60, the excess will overflow through tube 61. Water passing through restrictive capillary 62 or through overflow tube 61 enters tube 58 at opening 65 and is discharged to ground.

Figure 6:
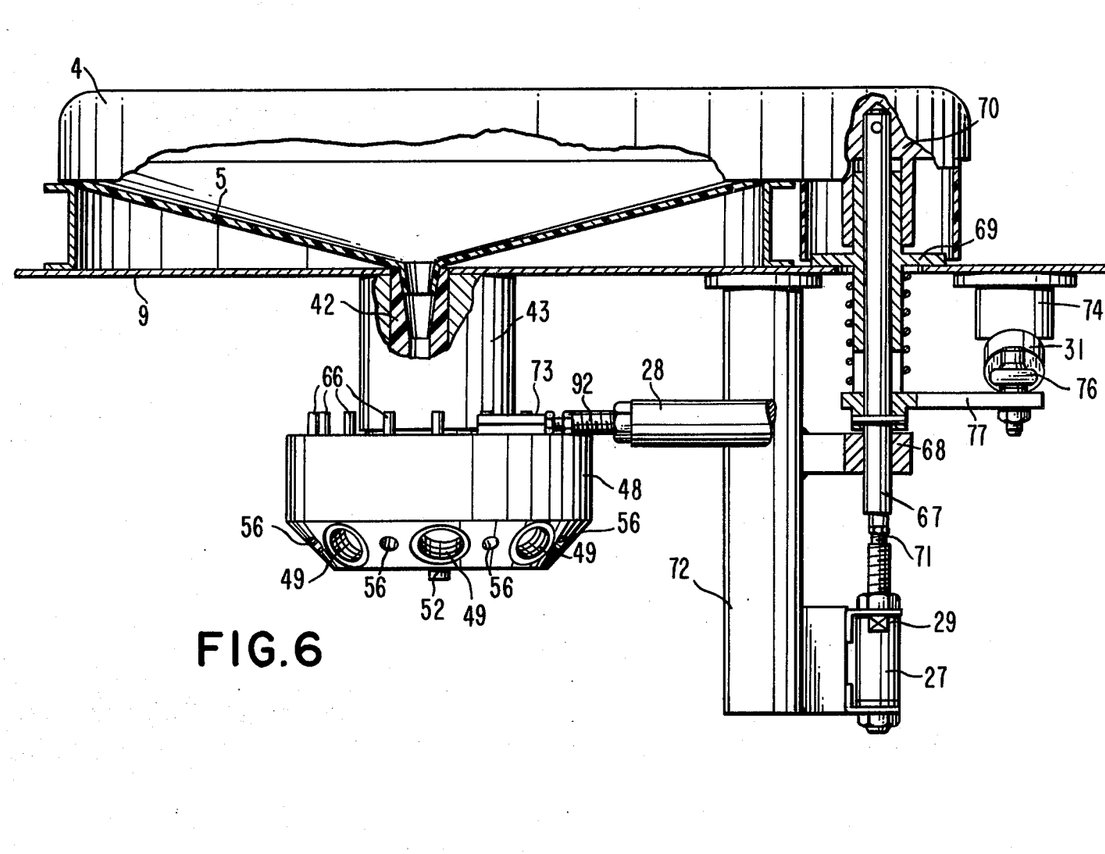
FIG. 6 is a partially sectioned view of the cover lift mechanism.
Figure 7:
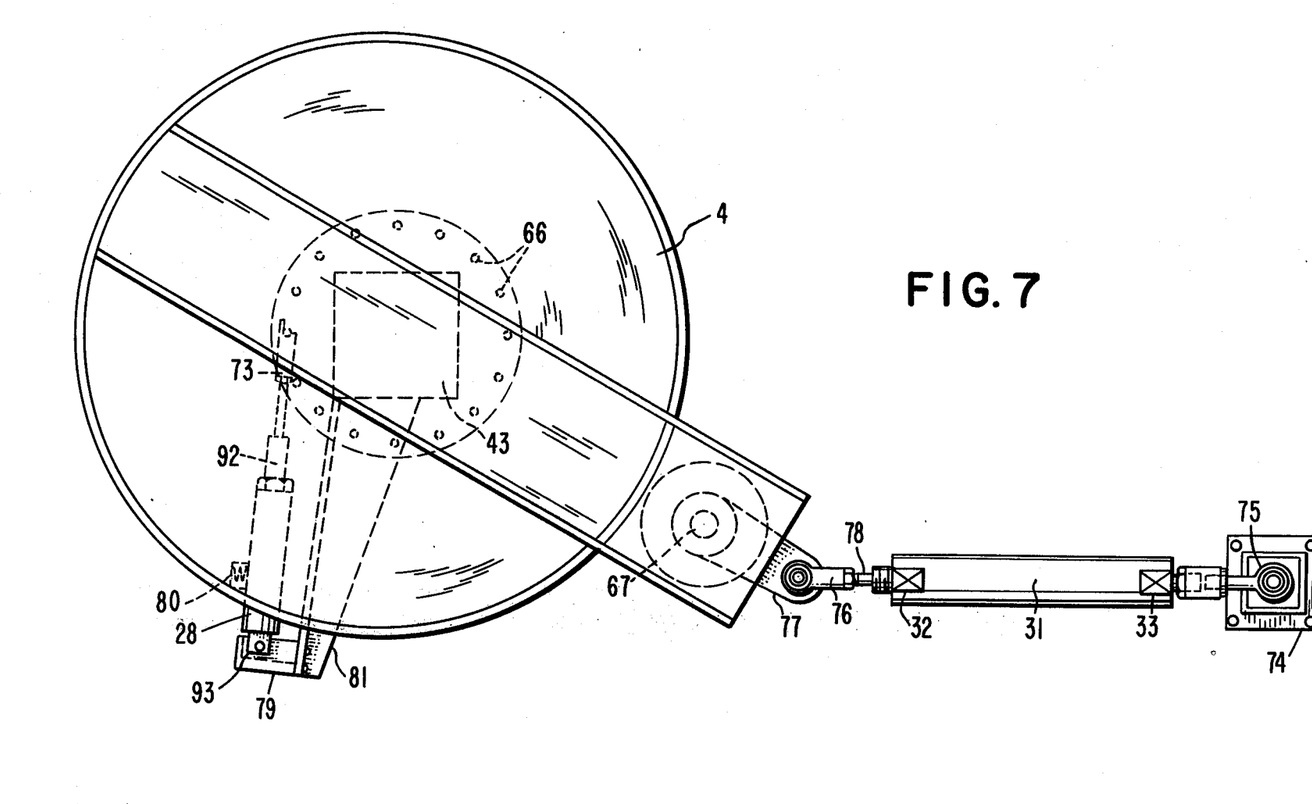
FIG. 7 is an overhead view showing the sample collection cover in a closed position over the turret mechanism.
Figure 8:
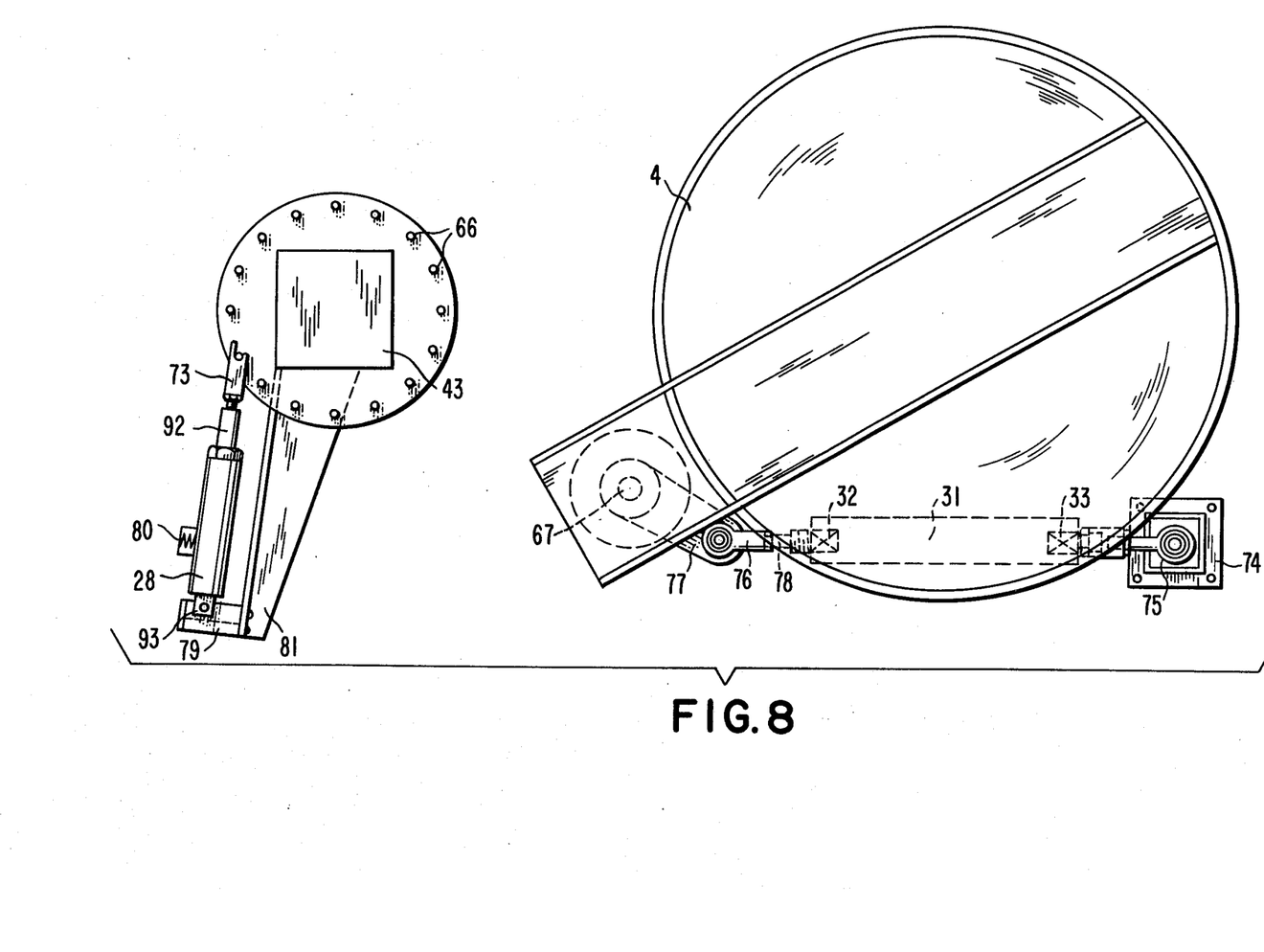
FIG. 8 is an overhead view of the sample collection cover in an open position to allow for precipitation detection and shows turret rotation relative to FIG. 7.

FIGS. 6, 7 and 8 illustrate the actuating mechanisms. Cover lift cylinder 27 is attached to cover shaft 67 which passes through bearings 68 and 69. The complete cover lift mechanism is attached to support post 72. The top of the cover shaft 67 is attached to cover bearing 70 which fits over bearing 69 to make a water protected seal. When the cover lift cylinder 27 is activated, rod 71 moves upward raising the sample collector cover 4 so that it clears the sample collection funnel 5. When cylinder 27 completes its upward stroke, it opens switch 29, shown as a rotation cylinder air switch allowing cylinder 31 to rotate raised cover.

Turret rotation penumatic cylinder 28 is actuated simultaneously with the cover lift cylinder 27. The extension rod 73 attached to the rod 92 of cylinder 28 is designed to engage turret index pins 66 as the rod moves forward. This action causes the turret to rotate one-sixteenth of a complete rotation each time the rod 92 of cylinder 28 is actuated.

FIGS. 7 and 8 are overhead views of the cover rotation and turret rotation mechanisms. Cover rotation cylinder 31 is attached to support block 74 by swivel connector 75. The rod 78 of cylinder 31 is attached by swivel connector 76 to arm 77 which is attached to cover shaft 67. When the cover 4 is raised, the switch, e.g., an air switch, activates cylinder 31 and rod 78 moves forward causing the cover to rotate about 120° from the initial closed position of the cover over the collecting funnel as demonstrated in FIG. 7 to the open cover position demonstrated in FIG. 8. Cover open limit switch 32 shows as a magnetic reed switch attached to cylinder 31 closes when rod 78 is fully extended signalling the controller that the cover is fully rotated. The controller de-energizes solenoid valves 26 and 30. Rotation cylinder 31 is supplied by a four-way solenoid valve 30 and hence pressure is maintained to hold the piston rod in the extended position. Cylinders 27 and 28 are supplied by a three-way solenoid valve which causes these cylinders to vent to the atmosphere when the valve is de-energized. Both cylinders are of the spring return type and thus the cover drops as rod 71 as shown in FIG. 6 moves downward and extension rod 73 retracts from the extended position demonstrated in FIG. 7 to the withdrawn position as demonstrated in FIG. 8. Spring 80 pushes the turret rotation pneumatic cylinder 28 in toward the cylinder support bracket 81 to permit extension rod 73 to align with the next turret index pin. Cylinder support block 79 contains a swivel mount 93 for cylinder 28 permitting the slight rotation necessary from the spring action. The cylinder support mechanism is attached to turret support block 43.

Figure 9:
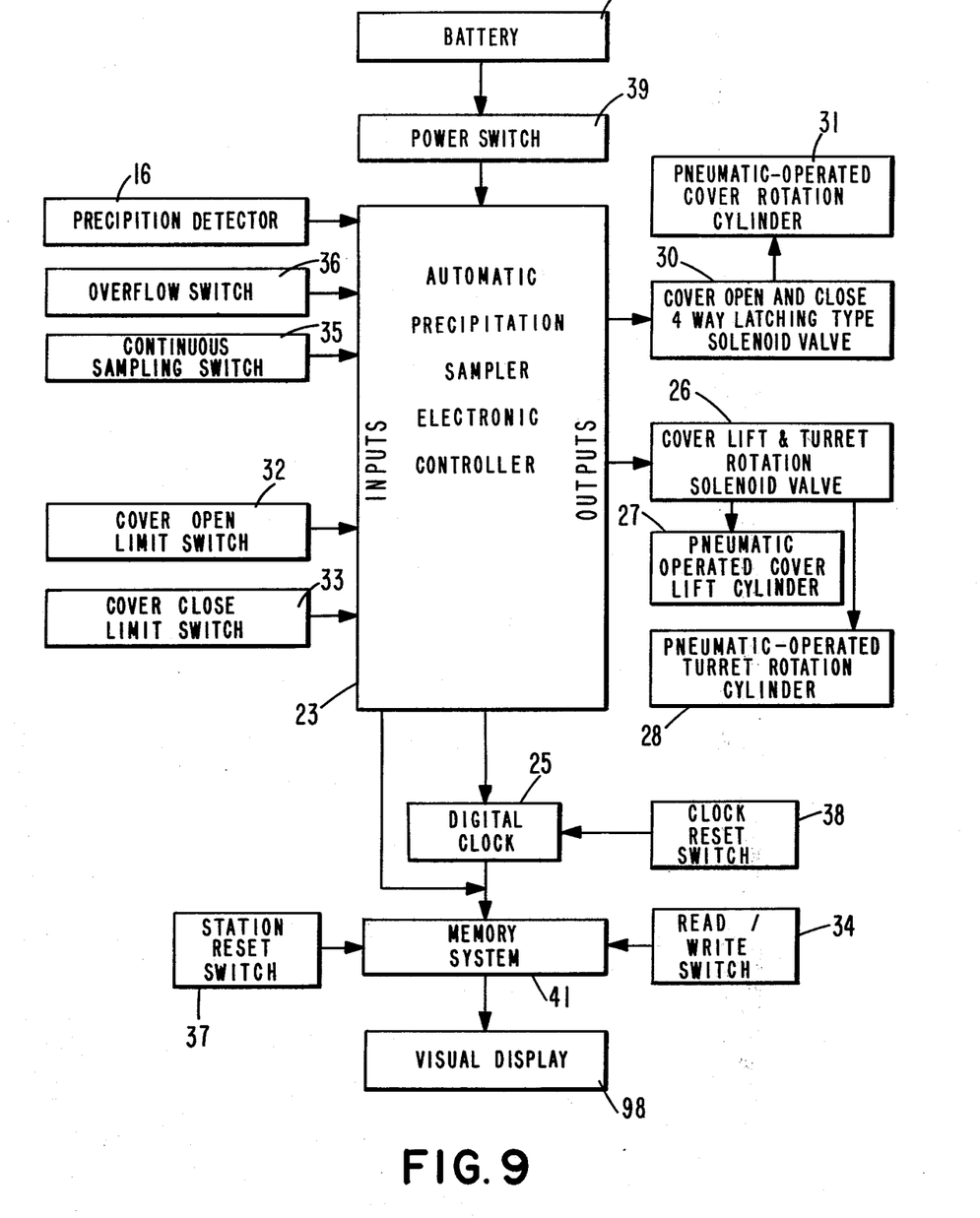
FIG. 9 is a block diagram showing the interrelation between the sensing switches which provide input information to the electronic control unit and the actuating elements of the system which respond to output signals from the controller.

FIG. 9 is a block diagram which shows the interrelation between the sensing switches which provide input information to the electronic control unit 23 and the actuating elements of the system which respond to output signals from the controller. The controller is powered by a battery 24 controlled by a power switch 39 and outputs to a digital clock 25 and memory system 41 which records the time at which each sample was collected and also the sample position on the collection turret.

Figure 10:
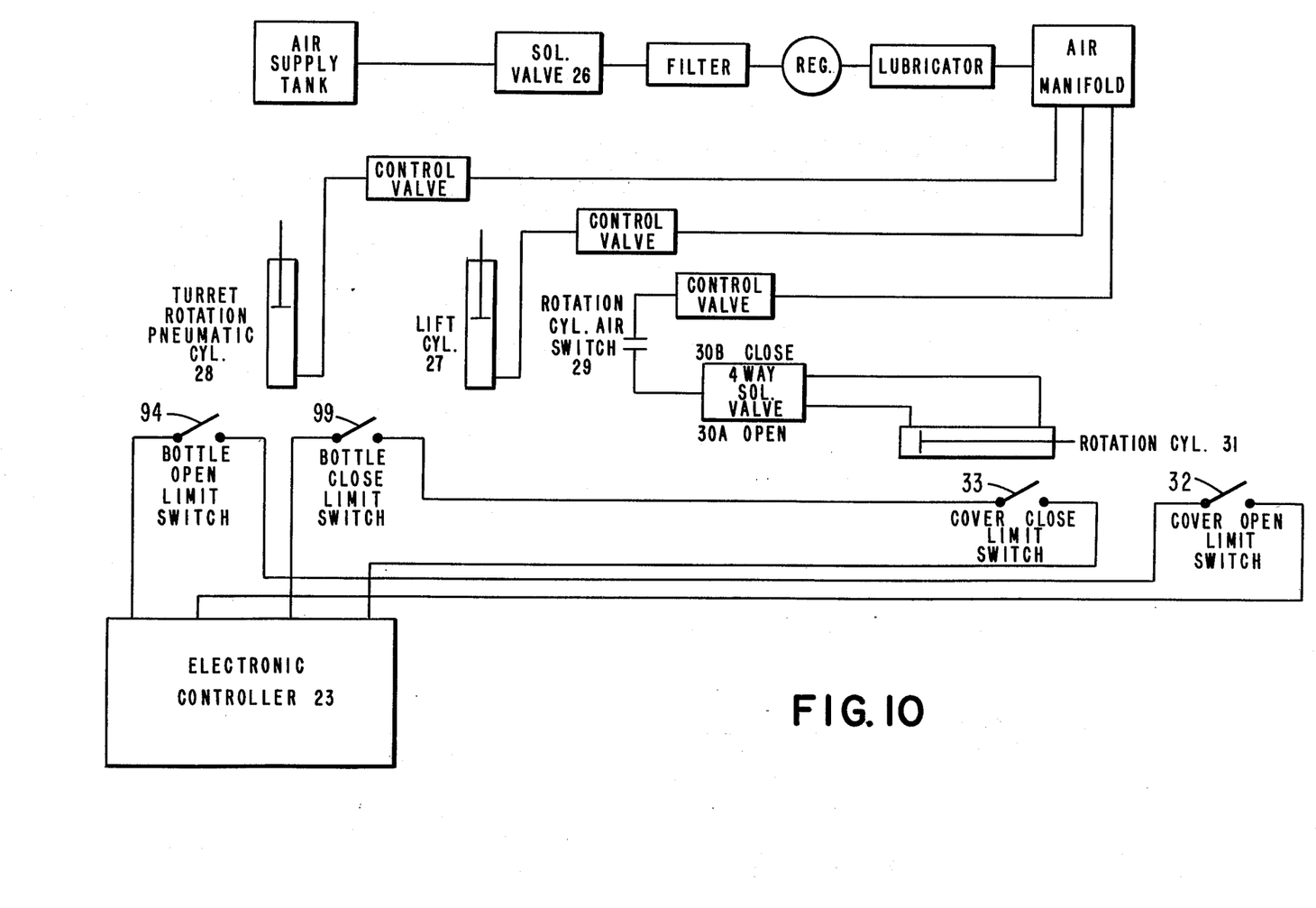
FIG. 10 is a schematic of a pneumatic operating system for controlling the operation of the sample collection system.

With reference to FIGS. 9 and 10, when precipitation detector 16 is actuated, controller 23 actuates the air supply solenoid valve 26 and the four-way solenoid valve 30A. This action permits compressed gas to flow to the cover lift cylinder 27 and to the turret rotation penumatic cylinder 28. The turret rotation penumatic cylinder 28 produces a partial rotation of the sample turret, causing a sample bottle to move into a collection position and the closing of the bottle open limit switch 94. The action of the cover lift cylinder 27 causes sample collector cover 4 to rise and when the action is complete, to open air switch 29 which allows air to flow to four-way valve 30A and allows the rotation cylinder 31 to open, causing the cover to rotate about 120° from its initial position directly above sample collection funnel 5. When the cover is fully rotated, the cover-open limit switch 32 is closed signalling controller 23 that the sample collection funnel 5 is completely uncovered. The controller 23 then de-energizes the solenoid valves 26 and 30A which permit gas to escape from the cover lift cylinder 27 and the turret rotation pneumatic cylinder 28. The result is that both cylinders return to the retracted position by spring action; thus the cover drops and the turret rotation cylinder resets such that the next rotation of the turret can be made when called for.

With reference again to FIGS. 9 and 10, the complete action of the automatic precipitation sampler can be described. An earlier section described the sequence of events leading to uncovering the sample collection funnel 5 following detection of precipitation. When precipitation detector 16 signals that rain has ceased, the controller 23, then actuates solenoid valves 26 and 30B. Valve 26 is energized causing the cover to lift, the turret to move to the next position, and close the bottle close limit switch 99. When the cover is raised, air switch 29 is opened and causes air to flow through four-way solenoid valve 30B which causes rotation cylinder 31 to retract thus closing cover 4 and the cover close-rotation-limit switch 33. When cover close-rotation-limit switch 33 and the bottle-close limit switch 99 are closed, the controller de-energizes solenoid valves 26 and 30B causing the cover to drop and the turret rotation cylinder to retract. A mechanical means is provided to prevent rotation of the cover while it descends over the collection funnel.

Each time the controller engergizes solenoid valve 26, it also signals the clock circuit to store the accumulated time and turret index number in memory circuit 41. This action is followed by an incrementing of the index number and a continuation of time accumulation in the clock register circuit. (The stored results may be retrieved at any time by selecting "Read" on the Read/Write switch 34 which causes a visual display 98 to be activated. The index numbers and associated stored activation times are then sequentially displayed at 9 second intervals.) The index position number and accumulated time can be reset to zero by closing switches 37 and 38 respectively.

The automatic precipitation sampler is designed to collect one sample from each precipitation event; however, by closing continuous sampling switch 35, it is possible to collect as many as eight separate samples from a single precipitation event. Closing the continuous switch brings into action overflow pressure switch 36 which closes shortly after a sample bottle fills. The controller 23 senses this as a cessation of precipitation and proceeds to cover the funnel and rotate the full bottle to the next position. A drain tube moves into the collection position causing accumulated water in the turret and funnel to run out quickly. The overflow pressure switch soon opens again since the supply of water has ceased. If precipitation is continuing, pressure switch 16 is still closed causing the controller to initiate action to uncover the funnel again and to move another sample bottle into a collection position. This action will repeat until all bottles are filled if precipitation is heavy and continuous for sufficient time. Each time the turret moves, the clock results are stored as in the case of the non-continuous mode of sampling. The controller prohibits further movement of the turret or other action of the sampler when index position 16 is reached.

When temperatures are low enough that precipitation falls as snow, in order to utilize the present invention both the open cylinder precipitation detector 3 and the sample collection funnel 5 must contain heating elements, located so that the precipitation is converted to and remains water at least until its enters the sample storage means. Preferably, these heating elements are affixed to the under surface of both the precipitation detector and the collection surface and are automatically energized through the use of a pre-set thermal switch when the outside air temperature falls to a level low enough to cause precipitation to fall as snow or freezing rain.

Figure 11:
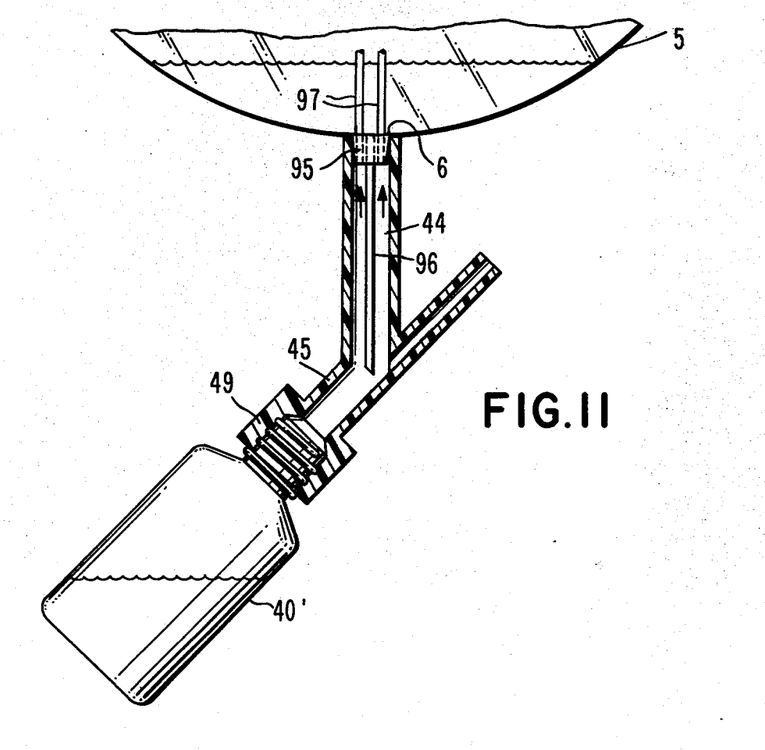
FIG. 11 is a schematic view of an air release mechanism in the water flow passage to prevent air locking in the sample collector.

As shown in FIG. 11, if desired a vent system can be installed in the collection funnel opening 6 to aid in preventing air locking of the system especially during heavy precipitation events. A Teflon stopper 95, equipped with air outlet tubes 97 and precipitation inlet tube 96 allows air to flow out of bottle 40 as the bottle fills.

It will be appreciated that many variations for mechanisms required to produce the required movements exist (such as commonly available precipitation detectors) and could be substituted for the system described. It will also be appreciated that many kinds of electronic logic systems can be designed to carry out the control function and that a larger system containing more sampling stations could be obtained by a simple scale-up of the automatic precipitation sampler as described.

While the wetted surfaces of the device have been described as comprising Teflon, a polyfluorocarbon, the wetted surfaces can be formed from or coated with any otherwise suitable material which is relatively inert, that is does not contaminate the precipitation collected and stored in a manner which affects the validity of the analysis intended to be conducted.

While the preferred embodiment of the invention has been illustrated and described, it will be understood that various modifications may be made without departing from the spirit of the invention as defined in the following claims.

What is claimed is:

1. An automatic precipitation sampling device comprising:
   (a) a precipitation collection surface having a removable cover means thereon,
   (b) a precipitation detection means which detects precipitation, operably associated with said removable cover means to cause said cover means to be removed from precipitation collection surface during precipitation, and to cause said cover means to recover said precipitation collection surface upon the cessation of precipitation, or when a predetermined amount of precipitation is collected,
   (c) a plurality of precipitation sample storage means,
   (d) precipitation sample distribution means in fluid communication with said collection surface and one of said sample storage means for transporting a precipitation sample from said collection surface to said one sample storage means,
   (e) means for sequentially positioning each of said sample storage means in fluid communication with said distribution means,
   (f) means operably associated with said means for sequentially positioning said sample storage means whereby the positioning of said sample storage means is regulated in relation to separate precipitation events or to predetermined segments of the same precipitation event,
   (g) means for sealing the sample storage means when not in fluid communication with said distribution means,
   (h) means for measuring and recording the chronological time and lapsed time for one or more of the operations conducted by the apparatus,
   (i) all the precipitation wetted collection distribution and storage surfaces being formed from a relatively inert material.

2. A precipitation sampling device, as in claim 1, in which the precipitation detection means comprises:
   (a) a precipitation collection means containing a flow restrictive element which restricts the gravity flow of precipitation collected, and
   (b) sensing means which senses a predetermined amount of precipitation retained by said flow restrictive elements, (c) means operably associated with said sensing means for signalling the presence or absence of said predetermined amount of precipitation.

3. A precipitation sampling device, as in claim 1, where said removable cover which is initially in a sealed relationship over said precipitation collection surface is lifted from and rotated clear of said precipitation collection surface upon a signal from said precipitation detection means and is returned over and into a sealed relationship with said collection surface upon a further signal from said detection means as a predetermined signal.

4. A precipitation sampling device, as in claim 1, where said means for sequentially positioning said sample storage means comprises a rotatable turret containing means for removably holding a plurality of sample storage means in a manner such that the all but one of said plurality of sample storage means is sealed, while said one storage means in a position to receive a precipitation sample.

5. A precipitation sampling device, as in claim 1, wherein said measuring and recording means measures and records the time at which a sample storage means is positioned in fluid communication with said distribution means, the time said sample storage means is positioned in a sealed position, and the identity of said sample storage means.

6. A precipitation sampling device, as in claim 1, wherein all power requirements are supplied by a self-contained source.

7. A precipitation sampling device, as in claim 1, containing means for maintaining precipitation wetted surfaces above freezing temperature when the ambient temperature is below freezing.

* * * * *